United States Patent [19]

Siclari et al.

[11] 3,947,276

[45] Mar. 30, 1976

[54] METHOD FOR THE PRODUCTION OF CELLULOSE-BASED FIBRES AND POLYNOSIC FIBRES HAVING A HIGH RESISTANCE TO COMBUSTION, AND FIBRES AND TEXTILE ARTICLES OBTAINED THEREBY

[75] Inventors: Francesco Siclari, Barlassina; Pietro Paolo Rossi, Garlasco, both of Italy

[73] Assignee: Snia Viscosa Societa' Nazionale Industria Applicazioni Viscosa S.p.A., Milan, Italy

[22] Filed: Oct. 24, 1973

[21] Appl. No.: 409,070

[30] Foreign Application Priority Data

Oct. 26, 1972   Italy................................ 30978/72

[52] U.S. Cl................ 106/15 FP; 106/168; 8/181
[51] Int. Cl.$^2$........................ C08L 1/24; C09D 5/18
[58] Field of Search............. 706/15, 168; 264/194; 260/121; 8/116 P, 181; 106/168

[56] References Cited
UNITED STATES PATENTS

| | | | |
|---|---|---|---|
| 2,345,345 | 3/1944 | Koch.................................. | 264/194 |
| 2,768,997 | 10/1956 | Reeves............................... | 260/121 |
| 2,809,941 | 10/1957 | Reeves et al. ....................... | 8/116 P |
| 3,645,936 | 2/1972 | Gardner.............................. | 8/181 |
| 3,704,144 | 11/1972 | Toy et al............................ | 264/194 |

*Primary Examiner*—Theodore Morris
*Attorney, Agent, or Firm*—Shlesinger, Fitzsimmons & Shlesinger

[57] ABSTRACT

A method is disclosed for producing cellulosic and/or polynosic fibres having flame-resisting properties, the improvement consisting in the fact that a composite viscose is spun in an acidic bath, said composite viscose being obtained by the association in an aqueous solvent, of cellulose xanthate with a phosphorus and nitrogen compound, dissolved in the same aqueous solvent and capable of being converted, while cellulose is being regenerated in said acidic bath, into a state of substantial insolubility. The phosphorus and nitrogen compound is a compound obtained by reacting a phosphonium derivative with aminoacids and amines and/or ammonia. A preferred compound is tetrakis-hydroxymethylphosphonium chloride. By so doing, an efficient flame-retarding protection is obtained for the fibre without sacrificing the physical properties thereof. Critical quantities, reaction conditions and test results are reported.

13 Claims, No Drawings

METHOD FOR THE PRODUCTION OF CELLULOSE-BASED FIBRES AND POLYNOSIC FIBRES HAVING A HIGH RESISTANCE TO COMBUSTION, AND FIBRES AND TEXTILE ARTICLES OBTAINED THEREBY

This invention relates to a method for the obtention of fibres and textile articles having a predominantly cellulosic nature, more particularly fibres and yarns or regenerated cellulose (Viscose rayon) obtained by wet spinning, in acidic baths, of cellulose as treated with carbon disulphide, and having a high resistance to combustion and to the retention of an incandescent condition. This invention also relates to the articles obtained by carrying said method into practice, that is to say, fibres, yarns and artifacts of a textile nature which, at least partially, are formed by cellulose fibres having a high resistance to combustion while concurrently exhibiting homogeneousness, brightness, hand and other features which are practically equal or at least much similar to those possessed by the fibres, yarns and artifacts which are entirely composed by cellulose and thus, as is well known, easy to be inflamed and highly combustible.

The problem of reducing the combustibility of textile cellulosic or polynosic products as made artificially, especially with a view to preventing fire hazards and their feed and propagation has been considered long since in the appertaining art. Numerous approaches have been suggested and adopted in order to minimize to a greater or lesser degree, the high flammability and combustibility of the textile products formed by, or predominantly containing, regenerated cellulose fibres. The approaches which have led to the obtention of practical and efficient results essentially comprise the addition to the fibres, the artifacts and also the spinnable alkaline viscose solution, of products which either retard or inhibit the combustion, the so-called "anti-flammability additives".

According to the conventional art, the anti-flammability additives which are regarded as the most efficient are the compounds or the combinations of compounds containing phosphorus and nitrogen. Compounds which are widely used are tetrakis-hydroxymethylphosphonium chloride and hydride (see for example the U.S. patent specification No. 2,772,188). These and other compounds, in the solid state and made nonsoluble (a condition which is imperative to ensure their persistance to washing of the articles and subsequent different conditions of treatment and use) can be applied, in the state of powders having the finest possible grit size, both as a consequence of surface treatments of the spun product, and by adding them to the spinnable viscose solution.

In the former case, even applying considerable amounts of additives to the surface of the product, to the prejudice of softness, brightness and hand of the artifact being obvious, the flame resistance properties are attenuated and may even disappear with the lapse of time under the action of rubbing and external agents. In the latter case, even providing to the cumbersome operation of very fine grinding of the solid additive, the particles which form the latter are in any case heterogeneous elements in the fibres, which can be clearly seen by the easiest microscopical investigations and mat the fibres and the filaments and suppress the brightness.

The introduction of these additives to the mass of spinnable viscose, in addition, is conducive to the occurrence of other serious problems and shortcomings. In the first place, it is extremely difficult to obtain an even distribution in actual terms of the particles of the additive in the viscose mass. These particles cause clogging of the filters and the spinning nozzles, especially in the production of fine-denier fibres, which are the ones most frequently required by the manufacturers.

Moreover, the physical presence of the foreign matters as materialized by the additive particles, locally prejudices and to a much variable degree the mechanical resistance of the yarns especially when it is a fine-denier yarn, since it occupies a portion of the cross-sectional area thereof, and/or causes its local bulkiness. In addition, these particles are prone to migration towards the surface, the result being the possibility of removal.

In order to suppress at least partly these serious drawbacks and others, the addition has also been suggested of compounds which are insoluble in the liquid state or the oily state (see for example the U.S. patent specification No. 3,455,713). These additives, whose particles or droplets are obviously susceptible of being deformed or stretched during progress of spinning and drawing, are always foreign matters and may lead to the occurrence of the attendant disadvantages.

Considering now the improvement of the flame-resistance properties, such an improvement can be regarded, with a rough estimate, as being proportional to the quantity of the additive which is introduced, in terms of its phosphorus contents and nitrogen contents, as compared with the cellulose contents of the fibre. The long experience in the art has permitted to confirm that a fair resistance to flaming requires, as a rule, the presence of about 3% of phosphorus and about 2% nitrogen on a weight basis with respect to the cellulose.

A few experimental tests have been suggested and standardized for evaluating the degree of non-flammability. One of these tests is the so-called "vertical flammability tests" (according to the AATCC 34/1966 specification) and during this test a fabric sample is exposed to the flame of a Bunsen burner during 12 seconds and the duration of the possible continuation of the combustion of the sample is measured, after having removed the flame. A severe test is the "45° test" in which the sample is exposed to the flame and maintained to such an inclination. These tests are regarded as having been "passed" when the flame is extinguished during a period of 3 to 5 seconds. Account is also taken of the persistence of the incandescent state upon extinction of the flame. As a matter of fact, a "post-incandescence" may prove to be a great hazard, for example in fires which burn in the presence of wind and airstreams capable of conveying incandescent particles into contact with other combustible materials, even located far away.

Obviously, the degree of resistance to the flame, which most advantageously should be conferred to the cellulose-based products, especially for textile applications, can be well different according to the use and the service conditions of the articles of manufacture. For example, in fabrics for table-cloth articles and the like, passing of less severe tests or even the absence of the post incandescence can be regarded as sufficient. For articles of apparel and bed linen it is advantageous and desirable to achieve a greater resistance to combustion, whereas for curtains and similar articles the resistance in question should desirably be very high. Thus the resistance to flame is a desirable property whose degree can, however, be different, so as to obtain the most favourable trading off between the desirable property in point and the tensile, elongation and other physical properties, which are unavoidably prejudiced, to a correspondingly variable degree, by the presence of additives and/or the performance of treatments tending towards imparting to the fibres and thus to the articles the expected resistance to combustion.

The present invention has for its object the solution of the technical problems enumerated above, with modes of operation and means which are mainly directed towards the practical suppression of the heterogeneousness condition in the cross-sections and/or the surfaces of the fibres, which is considered by the present art an unavoidable result of the addition, no matter how performed and irrespective of the state of aggregation, of the antiflame additives, towards the obtention of fibres, yarns and articles in which the cross-sections of the mainly cellulosic structure do not exhibit any perceptible physical solutions of continuity, even including phosphorus and nitrogen compounds in the amounts which are required for obtaining, to the desired degree, said desirable properties of spontaneous stoppage of a combustion as possibly primed by a flame and/or the absence of post-incandescence.

Essentially, according to the invention, the method comprises the steps of associating to the spinnable solutions of alkali cellulose or to spinnable cellulosic viscoses, compounds of phosphorus and nitrogen which fulfil the following requirements:

a. That as a result of such association they be virtually soluble in the solvent of the alkali cellulose as treated with carbon disulphide, that is in said spinnable viscose, and b. that they be susceptible of taking up, during progress of regeneration of cellulose in the acidic spinning and coagulation bath, a state of substantial insolubility.

The result is that the first of these conditions, (a), is conducive, in practice, to a rapid and even dispersion to a molecular level of both the phosphorus and the nitrogen, or of the phosphorus- and nitrogen- containing groups, in the spinnable viscose, the state of solid solution in the yarn thus obtained being accordingly retained, whereas the second condition, (b) ensures the persistence of the combustion-inhibiting or retarding agents in the same yarns and in the articles of manufacture obtained by using the same.

Another object of the invention is thus to identify, to prepare and to use the compounds fulfilling the above enumerated conditions, more particularly those which can be easily obtained by adopting preparation runs which are comparatively quick and economically acceptable.

A further object of the invention is to provide a compound fulfilling the above indicated requirements and which can easily be associated to the cellulose-based viscose in the form of an alkaline solution, that is, a co-spinnable and co-coagulable which can be co-precipitated and co-solidified with said viscose. The spun and coagulated product thus obtained is, therefore, not entirely a cellulosic product, but it is not even a physically heterogeneous product such as it would be obtained by applying the known technology of the addition of the flame-inhibiting additives in the insoluble form already as they are added to the cellulosic viscose. The Applicants have no notice that there exists, in the terminology of the art, a definition which could properly be applied to the products as obtained according to this invention. These products could be defined and identified by an expression such as "combustion resistant modacellulosic fibre", the Applicants being in no wise bound to the appropriateness of such an expression.

According to the invention, said compound is obtained by preferably treating a derivative of tetrakis-hydroxymethylphosphonium, more particularly its chloride or hydroxide, so as to obtain an alkaline solution of the salt of a phosphorus containing product as obtained from the reaction of the phosphorus compound with aminoacids and with amines and/or ammonia, the reaction being preferably carried out with an alkali metal salt, preferably a sodium salt, of said aminoacids.

As aminoacids there can be used, for example, glycocoll (aminoacetic acid), sulphanylic acid, p-aminobenzoic acid, and the n-amino-1-oic acids, such as 12-aminododecanoic and 6-aminoesanoic acids, valine (alpha-aminoisovaleric acid), alanine (alpha-aminopropionic acid). As amines there can be used for example monoethanolamine, diethanolamine, cyclohexylamine, and ethylenediamine.

These reaction products, soluble in the aqueous solutions of alkali metal compounds, and thus in the spinnable solution of cellulose xanthate, undergo, in the cellulose regeneration bath, an acidifying and insolubilizing process which could be compared with that which cellulose itself undergoes, thus completing the process of homogeneous association in the spun cellulosic product, which can be used in the textile field.

The quantitative ratios between the cellulosic and the phosphorus containing components, respectively, in the form of their respective co-spinnable, co-coagulable and insolubilizable viscoses, are obviously varied according to the desired degree of the combustion resistance properties, (a degree which can also be expressed in terms of percentage of phosphorus and nitrogen, with respect to cellulose, as found by analysis in the end product). This association is preferably effected by injecting the alkaline solution of the phosphorus-containing compound in the flow of the cellulose xanthate solution, immediately upstream of the spinning nozzles, the ratios between the quantities of the two co-spinnable solutions being warranted by the use, as is conventional in the art, of appropriate metering pumps.

The physical performance of the association as effected virtually immediately before spinning is an asset since the ratios relative to carbon disulphide, which can readily be absorbed by the solution of said compound, remain unaltered. If desired, the two solutions of the phosphorus-containing compound and the cellulose based compound can be associated and admixed beforehand, it being however advisable, in such a case, that the soluble compound which is a characteristic feature of the invention, be previously subjected to a saturation treatment with carbon disulphide.

Obviously, the selection of ratio between the two viscoses to be associated, is effected by taking into account both the proper ratios between the solvent and the solute in the two solutions, and the phosphorus and nitrogen yield at the end of the treatment, that is, of the ratio, as determined by experiment, between phosphorus and nitrogen as present in the compound to be associated and found, respectively, by analysis, in the final spun and coagulated product.

In order to prevent an exceedingly high dilution of the composite viscose as fed to the spinning nozzles, it is an advantage that the phosphorus-containing compound is prepared in the form of a fairly concentrated solution, preferably in the form of a 20% – 30% aqueous solution. For determining said ratio between the feeding rates of flow, and anyhow of association between the co-spinnable viscoses or solutions, it can be taken into account that, as a rule, the phosphorus and nitrogen yield (which, inter alia, is a function of the type of aminoacid and/or the amine which possibly has taken part to the reaction) is generally never below 50% and can be in the order of 70% – 90%, the selection of these aminoacids and amines being obviously a function not only of the advisability of achieving the most favourable yields, but also of other factors of a practical and economical nature, such as availability on the market, ease of handling and cost of the different starting compounds.

As a rule, the preparation of the phosphorus-containing compound is effected by reacting during a first stage the phosphonium (tetrakis-hydroxymethylphosphonium hydroxide or, preferably, chloride) with an aminoacid, by operating at a pH which can range between 3 and 8.5 approximately, and at a temperature which can be varied from 10°C to 60°C, preferably between 20°C and 40°C. It is advisable, through not critical, to work under an inert gas blanket, such as nitrogen. During a second stage, this first condensation product is caused to react with ammonia, in a direct fashion, that is, by adding ammonia to the condensate, or indirectly, by adding the condensate to ammonia, at a temperature which, in both cases, can range between 20°C and 50°C. In this connection, it is fitting to recall that, if one would operate at higher temperatures (such as 60°C and over) gelling phenomena might occur which would render the product unusable or at any rate would render it difficult to be employed.

It is preferred that, prior to passing to subsequent concentration and/or possible addition for example of carbon disulphide, a product-stabilization stage be carried out, with $H_2O_2$ or other suitable product. By employing hydrogen peroxide, one operates at a temperature from 10°C to 50°C and preferably from 20°C to 40°C, with amounts which may vary between 0.7 and 1.5 mols of the oxidizing agent to each atom-gram of phosphorus.

Upon addition of the oxidizing agent, the product is stable and can be heated even to 100°C or over without alteration thereof, and can be stored for a long time. The concentration of the product is then carried out, preferably under vacuum, and possibly the akaline solution of the phosphorus compound can be enriched with NaOH so that its free alkali content (which can be titrated, for example, with HCl and phenolphthalein) is equal or near (as a percentage concentration) to that of the cellulose xanthate solutions, to which it shall be associated.

These and other more specific features of the invention, along with the showing of its practicability and applicability to the end of achieving the indicated advancement in the appertaining art, will become apparent in the course of the ensuing detailed description of a few exemplary embodiments of this invention.

These examples are concerned with a possible preparation and production, on a near-industrial scale, of the compound and textile yarns according to the invention to show said applicability along with a set of tests and trials, especially on a laboratory scale, showing the width of the ranges of starting materials such as they can be used and a few variables in the relevant results.

EXAMPLE 1

Preparation of the alkaline viscose of the phosphorus-containing compound.

A 180-liter stainless steel autoclave adapted to polymerization reactions, equipped with a jacket for hot water circulation and cold water cooling, distillation column, vacuum pumps and thermometer probes, has been charged, under nitrogen atmosphere, with 37.4 kilograms of 80% tetrakis hydroxymethylphosphonium chloride and then with a solution of 6.150 kilograms of aminoacetic acid in 14.4 kilograms of 20% NaOH, and lastly 30.4 additional kilograms of 20% NaOH and 20 kilograms water. The temperature is maintained at 25°–26°C.

Immediately after, at a temperature of 20°–25°C and during 10 minutes, there are added 16.7 kilograms of 32% $NH_3$, while maintaining a maximum temperature of 41°–42°C. Upon completion of this addition, the mass is heated to 45°–46°C and this temperature is maintained during 2 hours.

The whole is then treated with 15.1 kilograms of 130-volume $H_2O_2$ and there are added 3 kilograms of 20% NaOH. Distillation under vacuum is then proceeded with until obtaining a 27% (approx.) viscose solution, formed by 82.450 kilograms of alkaline viscose.

The analysis has given the following results, expressed in percentages by weight on the viscose solution is obtained in the way described hereinabove.

| | | |
|---|---|---|
| P | = | 5.86 % |
| $N_2$ (total) | = | 5.47 % |
| $N_2$ (prim.amines) | = | 1.23 % |
| pH | = | 12.24 |

EXAMPLES 2, 3, 4 AND 5 AND COMPARISON

The viscose as obtained according to example 1 has been associated to a spinnable viscose of cellulose xanthate (8.4% of cellulose) as currently produced and used for the production of polynosic fibres. The mixture of viscose of the phosphorus-containing compound and the cellulose xanthate viscose has been fed to a wet spinning line, in acidic bath, working under conventional conditions, which are not modified with respect to those adopted for the production of polynosic commercial fibers having 100% cellulose.

The physical association of the two viscoses was effected immediately upstream of the spinneret, by feeding it independently with metering pumps, adjusted so as to obtain different feed ratios so as to obtain fibres having different phosphorus and nitrogen contents, in order to ascertain the combustion resistance properties, along with the principal physical specifications. The results of the most significant examples are set forth and comparatively tabulated in the following Table I, which includes also the mechanical specifications of the fibres, as similarly obtained at 100% of regenerated cellulose, and exhibiting the well known high combustibility and post-incandescence.

The examples tabulated in Table I are referred to fibres as produced in the fine denier rating of 6.5 deniers. These fibres and the yarns obtained thereby exhibited a brightness and general properties not dissimilar from those having 100% cellulose and their cross-sections did not show uneven elements when examined under the usual microscopic investigations. The homogeneousness of the fibre has been confirmed, moreover, by the fact that its mechanical specifications, and its cross-section, were uniform in each point of the yarn length (these conditions, as is known, are not exhibited by fibres having an improved resistance to combustion when produced according to the conventional technology of introducing the insoluble anti-flammable additives in the spinnable viscose and which introduce hetereogeneous elements in the fibres).

In Table I the first column shows, in grams of the solution of the phosphorus-containing compound, as fed to the spinneret, for 100 grams of 8.6% cellulose xanthate viscose.

In the second column there is indicated, as a percentage by weight, the cellulose contents of the dried fibre. In the other columns there are indicated:

The tensile and elongation data, as measured on the fibre conditioned according to the methods known in the art.

The quantity by weight of phosphorus and nitrogen as a total, identified in the analysis of the fibre.

The result, either positive or negative, of the conventional "vertical test" (AATCC 34/1966) and "45-degree tests" (AATCC 33/1962) and also the absence or presence of post-incandescence after the extinction of the flame.

achieved, considered as themselves, and which is a function of the conditions of use of the article concerned, in the fact that such a resistance, to the expected degree, is achieved in a homogeneous fibre which does not exhibit the well known and serious drawbacks of the cellulosic fibres which have been either treated with or supplemented with the known additives, and whose properties are retained unaltered in spite of external actions such as repeated washings and others, on account of the even dispersion at a molecular level of the anti-flaming agents in the product as obtained according to the invention. On the other hand, the solubility of the product associated with the regenerated cellulose in the solvent for the xanthate and the consequent evenness of the fibres thus obtained, permits to consider as practicable, in the case of exceptional requirements, to obtain fibres having a high contents of flame-inhibiting agents, when the interest in the resistance to combustion and also to ignition predominates over that in the mechanical specifications.

EXAMPLE 6

Production and use of a phosphorus-containing compound which contains carbon disulphide.

Examples 2 to 5 have indicated that the viscose which contains flame-inhibiting agents has been physically associated to the cellulose xanthate viscose, immediately upstream of the spinnerets. Such mode of operation does not involve any technical or production shortcomings and the even dispersion and dissolution of the phosphorus compound in the solvent for the spinnable solution did not give rise to defects. On the

TABLE I

| Example | Fed-In P. comp. g×100 g | Cellulose contents % | Physical specif. | | Analysis | | Test results | | post-incandescence |
|---|---|---|---|---|---|---|---|---|---|
| | | | Tensile g/den | Elongation % | Phosphorus % | Nitrogen % | Vertical in 4 sec. | 45-degr. in 4 sec. | |
| 2 | 3.1 | 93.5 | 1.55 | 18 | 1.5 | 1.01 | negative | negative | absent |
| 3 | 4.9 | 90 | 1.50 | 17 | 2.25 | 1.52 | negative | positive | absent |
| 4 | 6.9 | 86.6 | 1.20 | 16 | 3 | 2.02 | positive | positive | absent |
| 5 | 9.7 | 82 | 1.04 | 17 | 4 | 2.70 | positive | positive | absent |
| Comparison | — | 100 | 1.60 | 25 | — | — | negative | negative | present |

A scrutiny of Table I makes it conspicuous that, as it is otherwise apparently predictable on the basis of the current technical knowledge in the art, the flame resistance properties are increased somewhat proportionally to the increase of the phosphorus and the nitrogen in the fibres. Example 2, in practice, points out the minimum useful limit of the contents of anti-flaming agents which is necessary in order that an appreciable effect may be arrived at (disappearance of post-incandescence). Examples 3 and 4 indicate how it is possible actually to obtain articles of manufacture which, within the limits of the different service requirements, afford safety guarantees against the propagation of the flames in the case of fires and otherwise. The comparison between Examples 4 and 5 shows how to exceed the values of the contents of anti-flaming agents beyond a certain boundary could lead very often to an unnecessary sacrifice of the mechanical specifications of the fibres.

It is desired to recall, at any rate, that the essential advance brought by the invention to the current technology should be principally seen, rather than in the degree of the combustion resistance properties as other hand, it has been ascertained that the phosphorus and nitrogen compound is particularly prone to become associated to carbon disulphide. Thus, the preparation is also provided for a compound which has already been associated to the sulphide in question and can thus be associated in turn to the xanthate viscose a certain period of time after spinning.

To give an example of this modification of a possible way of carrying the invention into practice, 100 kilograms of the phosphorus-containing viscose as obtained according to Example 1 have been supplemented by 4 kilograms of NaOH in 6 liters of water. There have then been added 15.2 kilograms of carbon disulphide, with a vigorous stirring and at room temperature, stirring being continued until the disulphide absorption was completed. After 4 hours the colour of the solution was orange-red.

The solution was combined, in a conventional storage tank and in the ratio indicated in Example 4, to a 8.4% solution of cellulose xanthate.

After 6 additional hours, the mixed viscose thus obtained was fed to a conventional wet spinning line and 6.5 denier yarns were produced (as in Examples 2–5 and relevant comparison), the results upon conditioning being the following:

| Physical specifications: | Tensile strength | 1.15 grs/den. |
|---|---|---|
|  | Elongation | 17.5% |
| Analysis | Phosphorus | 3.2% |
|  | Nitrogen | 2.18% |

The yarn has given a positive result both in the 45° and the vertical test, no post-incandescence having been detected.

EXAMPLES 7–11

Experimental check of preparation and yields.

By adopting laboratory methods, several procedures have been experienced for the preparation of the phosphorus- and nitrogen-soluble compound which can be associated with the cellulose xanthate viscoses according to the invention and the phosphorus yields have been checked after such as association and coagulation in an acidic bath.

0.5 mol (119 grams) of tetrakis-hydroxymethylphosphonium chloride (hereinafter connoted for short by the symbol THPC as used in the current language of the art), dissolved to give a 80% solution in water, have been charged in a 1000-ml flask equipped with a stirrer, a thermometer, a dropping funnel and reflux condenser. Through the funnel and maintaining by cooling the temperature within the range from 18°C to 20°C, a 20% aqueous solution of NaOH is added until obtaining that the pH of the mixture attains a value of 8.5 – 9. The solution is brought to the temperature of 38°C and there maintained at such a value by cooling during progress of the addition, during a 20-minute period, of 74.9 grams of a mixture formed by 19.5 grams of aminoacetic acid, 10.4 grams NaOH and 45 grams of water.

By thin layer chromatography (a layer of silica gel G, ethanol as the eluant with water and formic acid) the analysis has been effected of the sample of the thusly obtained product. This analysis has shown the presence of traces only of free aminoacids and the possible reaction product thereof with formaldehyde from THPC thus confirming that the aminoacid has reacted with THPC as such.

The thusly prepared reaction mixture is firstly treated with 34.9 grams water and then with 53.2 grams of a 32% aqueous solution of ammonia, the temperature being limited by cooling to 41°–42°C. Such a temperature was maintained by heating from outside during one hour. On completion of this period of time, the reaction mixture is cooled to 25°C and, through the droping funnel there were added 51 grams of 33.4% hydrogen peroxide the temperature being checked so as never to exceed 35°–40°C.

Upon completion of this treatment, the reaction product was concentrated under vacuum until reducing it to the total amount of 258 grams, an aqueous solution of about 27% concentration being obtained, which was viscous, clear and with a faint straw-yellow hue.

The analysis of this viscous solution has given the following results, expressed as percentages by weight on the total of the 27% solution (approx.):

| Phosphorus | = 6% |
|---|---|
| Total Nitrogen | = 5.62% |
| Primary Amine N | = 1.2% |
| Ammoniacal N | = 0.028% |

In order to avoid the intricate and cumbersome wet spinning operations, with consequent installation lock up and their preparation to the different cases, the checking of the behaviour of the result of this product was carried out in the following way, as used in the experimental practice of the compounds intended for the production of man-made fibres.

Samples of the product were mixed, in variable quantities, so as to obtain different initial contents and ratios, as expressed in terms of weight of phosphorus charge with respect to the cellulose, with a spinnable alkaline solution of cellulose xanthate having a 8.55% solid content. With the mixtures thus obtained there were formed films by compression between glass plates, films which were then coagulated in a 45°C bath having a conventional composition (in grams per liter: $Na_2SO_4$ : 320 ; $H_2SO_4$ : 130 ; $ZnSO_4$ : 5.8) as the acidic spinning bath for cellulosic fibres. Upon washing of the thusly coagulated films during 6 hours in running water and drying in an oven under vacuum, the tests were performed and the results as set forth in Table II below were obtained.

TABLE II

| Example | Grams of charged P per 100 gr. cellulose | Weight increase per 100 gr. cellulose | Grs. of P found per 100 gr. cellulose | Grs. of N (tot.) found per 100 gr. cellulose | P yield % |
|---|---|---|---|---|---|
| 7 | 4.75 | 19.5 | 3.44 | 2.33 | 72.5 |
| 8 | 3.26 | 14.05 | 2.41 | 1.63 | 74.0 |
| 9 | 2.44 | 10.3 | 1.755 | 1.185 | 72.0 |
| 10 | 1.64 | 7.31 | 1.205 | 0.817 | 73.7 |
| 11 | 0.825 | 3.81 | 0.640 | 0.431 | 77.5 |

It can be observed in this Table that the phosphorus yield is constantly high, irrespective of the ratio at which the xanthate viscose and the phosphorus-containing viscose have been associated. The percentage variations of the yield, as listed in the appropriate column, are apparently independent of this ratio and are probably due to the unavoidable variables in the preparation and analysis.

EXAMPLES 12–16

Quantitative and qualitative tests with different aminoacids and amines, or without amines.

By operating the methods as indicated in Examples 7 to 11, a number of compounds have been prepared, by utilizing different aminoacids and different amines and also, in a few cases, without using amines at all. The reactants and the results of the measures and analyses as carried out are tabulated in the following Table III in which the quantities of the reactants in question are expressed in moles.

In this Table, due to space shortage, the aminoacids and the amines have been identified by literal symbols and numerals on the sides of the respective molar quantities, the meanings being as follows:

AMINOACIDS (g) Glycocoll (aminoacetic acid)
(a) 12-aminoundecanoic acid
(c) 6-aminohexanoic acid
(s) Sulphanylic acid
(b) p-aminobenzoic acid
(l) Alanine (alpha aminopropionic acid)
(v) Valine (alpha aminoisovaleric acid)

AMINES

1. Monoethanolamine
2. Diethanolamine
3. Cyclohexylamine
4. Ethylenediamine

In order to ensure a maximum comparability between the results, tetrakis-hydroxymethylphosphonium chloride (THPC) has been constantly used. The phosphorus compound, obtained as an aqueous solution, has been weighed and analyzed upon oxidizing evaporation of the excess ammonia.

TABLE III

| Example | THPC moles | Aminoacid moles | Amine moles | Ammonia moles | Solution obtained (g.) | Phosphorus (%) | Total Nitrogen moles | Aminic Nitrogen moles |
|---|---|---|---|---|---|---|---|---|
| 12 | 1 | 0.50 (g) | — | 2.08 | 428 | 7.25 | 1.97 | 0.45 |
| 13 | 1 | 0.52 (g) | — | 1.75 | 468 | 6.62 | 1.95 | 0.486 |
| 14 | 1 | 0.52 (g) | — | 1.50 | 518 | 5.98 | 1.83 | 0.262 |
| 15 | 1 | 0.52 (g) | — | 1.25 | 440 | 7.05 | 1.57 | 0.145 |
| 16 | 1 | 0.55 (a) | — | 2.28 | 1138 | 2.72 | 2.04 | 0.398 |
| 17 | 1 | 0.55 (c) | — | 2.34 | 494.8 | 6.25 | 2.11 | 0.42 |
| 18 | 1 | 0.55 (s) | — | 2.16 | 686 | 4.51 | 2.03 | 0.43 |
| 19 | 1 | 0.55 (b) | — | 2.16 | 710 | 4.36 | 2.01 | 0.44 |
| 20 | 1 | 0.55 (g) | 0.55 (1) | 1.33 | 430 | 7.20 | 2.22 | 0.37 |
| 21 | 1 | 0.55 (g) | 0.55 (2) | 1.60 | 460 | 6.75 | 2.46 | 0.43 |
| 22 | 1 | 0.275 (g) | 0.825 (1) | 1.33 | 500 | 6.20 | 2.09 | 0.395 |
| 23 | 1 | 0.52 (g) | 0.11 (3) | 2.34 | 546 | 5.68 | 2.01 | 0.42 |
| 24 | 1 | 0.52 (g) | 0.266 (4) | 2.34 | 485 | 6.40 | 2.14 | — |
| 25 | 1 | 0.48 (l) | — | 2.00 | 503.6 | 6.15 | 2.04 | 0.492 |
| 26 | 1 | 0.52 (v) | — | 2.00 | 512 | 6.06 | 2.03 | 0.536 |

Coagulation tests have been carried out under the conditions set forth in the description of the Examples 7 to 11, of all the products listed in Table III. The results of these tests, in turn, are set forth in the Table IV below.

TABLE IV

| Example | Charged Phosphorus grs. per 100 grs. cellulose | Weight increase grs. per 100 grs. cellulose | Found P grs. per 100 grs. cellulose | Found N grs. per 100 grs. cellulose | Phosphorus yield % |
|---|---|---|---|---|---|
| 12 | 4.4 | 19.2 | 3.4 | 2.3 | 77.2 |
| 13 | 5.9 | 20.0 | 4.0 | 2.7 | 67.8 |
| 14 | 5.9 | 17.3 | 3.5 | 2.4 | 59.4 |
| 15 | 5.9 | 18.3 | 3.0 | 2.1 | 50.8 |
| 16 | 3.3 | 22.2 | 2.8 | 1.9 | 85.0 |
| 17 | 3.8 | 19.7 | 3.1 | 2.1 | 81.6 |
| 18 | 5.8 | 33.0 | 4.3 | 2.9 | 74.0 |
| 19 | 5.8 | 35.5 | 4.8 | 3.3 | 82.8 |
| 20 | 5.8 | 14.3 | 3.1 | 2.1 | 53.5 |
| 21 | 5.8 | 15.9 | 3.1 | 2.1 | 53.5 |
| 22 | 5.8 | 12.0 | 2.5 | 1.6 | 43.1 |
| 23 | 5.8 | 19.0 | 3.9 | 2.6 | 67.2 |
| 24 | 5.8 | 23.6 | 3.9 | 2.7 | 67.2 |
| 25 | 5.8 | 22.4 | 4.5 | 3.1 | 77.6 |
| 26 | 5.8 | 22.5 | 4.4 | 3.0 | 75.8 |

The bodies of the invention in which on exclusive property or privelege is claimed are defined as follows:

1. A method for the production of fibres and yarns consisting prevailingly of cellulosic compounds having high resistance to the propagation and maintenance of combustion comprising
    adding to a spinnable cellulosic solution of xanthate of cellulose,
    the product of reaction with a compound selected from the group consisting of ammonia and amines of tetrakis-hydroxymethylphosphonium with a monomeric aminoacid selected from the group consisting of aminoacetic, sulphanylic, p-amino-benzoic, 12-amino-dodecanoic, 6-aminohexanoic, alpha-aminoisovaleric, and alpha-aminopropionic acid, in solution in an alkaline aqueous solvent,
    the compound of phosphorus in the last-named solution being enriched with NaOH until its free alkali content is near that of the solution of xanthate of cellulose to which it is added, and being soluble in said solution of xanthate of cellulose, and
    spinning the mixed solutions through nozzles in a regenerating and coagulating bath,
    said product in solution being added to said spinnable cellulose solution by feeding it in metered amounts upstream of the spinning nozzles.

2. A method according to claim 1 wherein said phosphonium compound is tetrakis-hydroxymethylphosphonium chloride.

3. A method according to claim 1, wherein said compound is added to the spinnable cellulosic viscose in such an amount that in regenerated cellulose phosphorus and the nitrogen are present, on analysis, in amounts by weight of from 1.5 to 4% and of from 1% to 3% approximately, respectively.

4. A method according to claim 1, wherein said compound is added to the spinnable cellulosic viscose in the form of an aqueous solution including carbon disulphide.

5. A method according to claim 1, wherein said compound is obtained by the reaction of the phosphonium compound with an amine selected from the group consisting of monoethanolamine, diethanolamine, cyclohexylamine and ethylenediamine.

6. A method according to claim 1, wherein the spinnable cellulosic viscose is mixed with a 20% to 30% aqueous solution of said compound.

7. A method for the production of fibres and yarns consisting prevailingly of cellulosic compounds having high resistance to the propagation and maintenance of combustion, comprising
  in a first stage reacting a phosphonium compound with a monomeric amino acid selected from the group consisting of amino acetic, sulphanylic, p-aminobenzoic, 12-amino-dodecanoic, 6-aminohexanoic, alpha-aminoisovaleric, and alpha-aminopropionic acids, in a second stage reacting the product obtained from the first stage directly or indirectly with ammonia,
  stabilizing the product from the second stage with an oxidizing agent,
  adding the stabilized product to a spinnable cellulosic solution of xanthate of cellulose in which said stabilized product is soluble,
  before adding the stabilized product to the cellulosic solution enriching the product with NaOH until its free alkali content is near that of the spinnable cellulosic solution to which it is to be added, and
  spinning the mixture through nozzles in a regenerating and coagulating bath,
  said stabilized product being introduced in solution into said spinnable cellulose solution by feeding it in metered amounts upstream of the spinning nozzles.

8. A method according to claim 7, wherein the first stage is carried out by working at a pH between 3 and 8.5.

9. A method according to claims 7, wherein the first stage is carried out at a temperature between 10°C and 60°C, and the second stage is performed at a temperature not exceeding 50°C.

10. A method according to claim 7, wherein the oxidizing agent is $H_2O_2$, and the second stage reaction is carried out at a temperature between 10°C and 50°C with quantities of the oxidizing agent ranging from 0.7 to 1.5 mols per atom-gram of phosphorus.

11. A predominantly cellulosic fibre for the production of yarns, fabrics and textile articles in general, obtained by spinning in an acidic bath a viscose containing a cellulose xanthate solution, and the product of reaction with a compound selected from the group consisting of ammonia and amines of tetrakis-hydroxymethylphosphonium with a monomeric aminoacid selected from the group consisting of aminoacetic, sulphanylic, p-amino-benzoic, 12-amino-dodecanoic, 6-aminohexanoic, alphaaminoisovaleric, and alpha-aminopropionic acids, in solution in an alkaline aqueous solvent, the compound of phosphorus in the last-named solution being enriched with NaOH until its free alkali content is near that of the solution of xanthate of cellulose to which it is added, and being soluble in said solution of xanthate of cellulose, to impart to said fibre, yarn, fabric or article of manufacture, improved combustion resistance properties, and wherein its content of regenerated cellulose is less than 95%.

12. A textile fibre according to claim 11, which
  irrespective of the possible presence of additives, contains regenerated cellulose in an amount not exceeding 93.5% of its total weight,
  and at least 1.5% and 1%, approximately, of phosphorus and nitrogen, respectively, and which
  exhibits a substantial homogeneousness in its cross-sections as seen in a simple optical microscopical examination in natural light.

13. A textile fibre according to claim 11, wherein its cellulose content is between 93.5% and 82%, by weight, its phosphorus content is between 1.5 and 4% by weight, and its nitrogen content is between 1 and 2.7% by weight.

* * * * *